(12) United States Patent
Seal et al.

(10) Patent No.: US 8,337,898 B2
(45) Date of Patent: Dec. 25, 2012

(54) FUNCTIONALIZED NANOCERIA COMPOSITION FOR OPHTHALMIC TREATMENT

(75) Inventors: Sudipta Seal, Oviedo, FL (US); Swanand D. Patil, Orlando, FL (US); Manas K. Haldar, Fargo, ND (US); Sanku Malik, West Fargo, ND (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/154,849

(22) Filed: Jun. 7, 2011

(65) Prior Publication Data

US 2011/0268662 A1 Nov. 3, 2011

Related U.S. Application Data

(60) Division of application No. 12/147,759, filed on Jun. 27, 2008, now Pat. No. 7,959,949, which is a continuation-in-part of application No. 11/412,665, filed on Apr. 27, 2006, now Pat. No. 7,727,559.

(60) Provisional application No. 60/946,815, filed on Jun. 28, 2007.

(51) Int. Cl.
*A61K 9/14* (2006.01)
*A01N 59/16* (2006.01)

(52) U.S. Cl. ........ 424/489; 424/410; 424/421; 424/427; 424/429; 424/617

(58) Field of Classification Search ........... 424/401, 424/421, 427, 429, 489, 617
See application file for complete search history.

(56) References Cited

U.S. PATENT DOCUMENTS

| | | |
|---|---|---|
| 7,534,453 B1 * | 5/2009 | Rzigalinski et al. .......... 424/617 |
| 2003/0187077 A1 | 10/2003 | Chane-Ching |
| 2004/0241206 A1 | 12/2004 | Ketelson et al. |
| 2006/0150526 A1 | 7/2006 | Ota et al. |

* cited by examiner

*Primary Examiner* — Michael G Hartley
*Assistant Examiner* — Jagadishwar Samala
(74) *Attorney, Agent, or Firm* — Allen, Dyer, Doppelt, Milbrath & Gilchrist, P.A.

(57) ABSTRACT

The invention provides a composition comprising a plurality of nanoceria particles, a sufficient amount of at least one inhibitor of human carbonic anhydrase II associated with said plurality of nanoceria particles, and a pharmaceutically acceptable carrier containing said plurality of nanoceria particles with associated inhibitor. One preferred inhibitor of human carbonic anhydrase II comprises 4-carboxybenzene sulfonamide. The disclosed composition is useful in treatment of glaucoma.

7 Claims, 6 Drawing Sheets

FUNCTIONALIZED NANOCERIA COMPOSITION FOR OPHTHALMIC TREATMENT

RELATED APPLICATION

This application is a division of U.S. application Ser. No. 12/147,759 which was filed on Jun. 27, 2008 now U.S. Pat. No. 7,959,949, and which claimed priority from U.S. provisional application Ser. No. 60/946,815, filed on Jun. 28, 2007, and a continuation in part of Ser. No. 11/412,665 filed on Apr. 27, 2006, now U.S. Pat. No. 7,727,559 issued Jun. 1, 2010.

STATEMENT OF GOVERNMENT RIGHTS

The investigation leading to this application was supported at least in part by a grant from the National Science Foundation. The government may, therefore, have some rights in the invention, as specified by law.

FIELD OF THE INVENTION

The present invention relates to the field of nanotechnology and, more particularly, to nanoceria particles which carry a medicinal drug.

BACKGROUND OF THE INVENTION

Countless individuals suffer from the ocular disease glaucoma. This condition describes a destruction of optic nerve cells and deterioration of eyesight as a result of increased intraocular pressure. The pressure is caused in part by a buildup of carbon dioxide in the eye. An enzyme that aids in the production of CO2 is human carbonic anhydrase II (hCAII). This $Zn^{2+}$ containing metalloenzyme (FIG. 1) catalyzes the reversible hydration of carbon dioxide to bicarbonate and is commonly found in living organisims.

Sulfonamide compounds have been shown to selectively inhibit hCAII even at low concentratons.[1] Therefore, inhibition of hCAII with sulfonamides constitutes one of the most physiological approaches for treatment of glaucoma. In 1958 Beasley et al. reported the in vitro binding of 4-carboxybenzene sulfonamide (CBS) to the carbonic anhydrase (CA) enzymes.[2] Since then, many other hCAII inhibitors based on this moiety have been reported.[3-5] A remarkable increase in the hCAII inhibition activity was observed for simple aliphatic esters of CBS.[5] Also, it is now extensively documented that significant enhancement of CA inhibition can be achieved through coupling the primary recognition aromatic sulfonamide motif with secondary binding elements.[3,5-9] The mechanism for inhibition of hCAII by CBS involves coordination of the sulfonamide group (as the anion) to the zinc atom in the active site of hCAII to form a complex in an exothermic reaction. 6, 10, 11.

In ophthalmic diseases such as glaucoma, treatment with conventional liquid eye drops is an inefficient mode of therapy because of lachrymal drainage losses. Because of the high elimination rate, only a very small amount of about 1-3% of the dosage actually penetrates through the cornea and is able to reach intraocular tissues.[12-14] Nanoparticles provide a promising potential as drug carriers for ophthalmic applications. The colloidal nanoparticles may be applied in liquid form just like eye drop solutions. After optimal drug binding to the nanoparticles, the ocular bioavailability of many drugs is significantly enhanced in comparison to normal aqueous eye drop solutions.[12] Also, smaller particles improve patient comfort during administration as a scratchy feeling tends to occur with larger particles. Nanoparticles and microspheres of various synthetic polymers such as poly-butylcyanoacrylate,[15,16] polylactic acid,[17] polymethylmethacrylate,[16] and so forth as well as natural biocompatible polymers like albumin [18,19] have been used for ophthalmic drug delivery applications.

SUMMARY OF THE INVENTION

With the foregoing in mind, in one embodiment, the present invention advantageously provides a composition comprising a plurality of nanoceria particles, a sufficient amount of at least one inhibitor of human carbonic anhydrase II associated with said plurality of nanoceria particles, and a pharmaceutically acceptable carrier containing said plurality of nanoceria particles with associated inhibitor. The at least one inhibitor of human carbonic anhydrase II preferably comprises 4-carboxybenzene sulfonamide. Preferably, the enzyme inhibitor is effective against human carbonic anhydrase II and the composition is used in treating an eye disease, particularly glaucoma, by contacting the eye with the composition.

The composition may also further comprise a detectable tag associated with the plurality of nanoceria particles. The skilled will recognize that the term "tag" indicates any atom or molecule which, when associated with the nanoceria, imparts a property which allows for tracking of the nanoceria during treatment. Tracking may be by any known method, for example, fluorescence responsive to ultraviolet light. In effect, the tag may be a fluorescent tag associated with said plurality of nanoceria particles and the fluorescent tag is preferably a fluorescein compound associated with said plurality of nanoceria particles, in particular, carboxyfluorescein.

In this preferred embodiment of the invention, the nanoceria particles are made by a method comprising a reaction according to Scheme 1A, shown in FIG. 3. Moreover, the nanoceria particles associated with carboxyfluorescein are made by a method comprising a reaction according to Scheme 1B in FIG. 3.

Another embodiment of the invention includes a composition comprising a plurality of nanoceria particles, a sufficient amount of at least one biologically active agent bound to said plurality of nanoceria particles, and a pharmaceutically acceptable carrier containing said plurality of nanoceria particles with bound inhibitor. Preferably, the biologically active agent comprises a medicinal drug and, particularly, an ophthalmically active drug, which could be an enzyme inhibitor. In particular, the biologically active agent could comprise a sulfonamide compound, especially one that inhibits human carbonic anhydrase.

Another preferred embodiment of the invention includes a method of treating a patient's eye condition. The method comprises providing a composition containing a plurality of nanoceria particles associated with a drug and suspended in a pharmaceutically acceptable carrier, and contacting the patient's eye with the composition.

In this embodiment, the drug preferably comprises an enzyme inhibitor and especially an inhibitor of human carbonic anhydrase. The eye condition comprises glaucoma and drug comprises 4-carboxybenzene sulfonamide. In the method, contacting the eye may be accomplished in any fashion known to the skilled but, typically would comprise a procedure selected from instilling, injecting, diffusing and combinations thereof.

Nevertheless, while this disclosure preferably comprises nanoceria compositions and treatments directed to eye conditions and, particularly, to glaucoma, the invention includes within its scope the concept of associating a drug with the nanoceria particles as carriers. The range of drugs that can be employed in the invention is rather broad and includes any drug or pharmaceutical composition that can be complexed, associated with or otherwise bound to the nanoceria particles without significantly adversely affecting the biological activity of the drug.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

Figure 1:
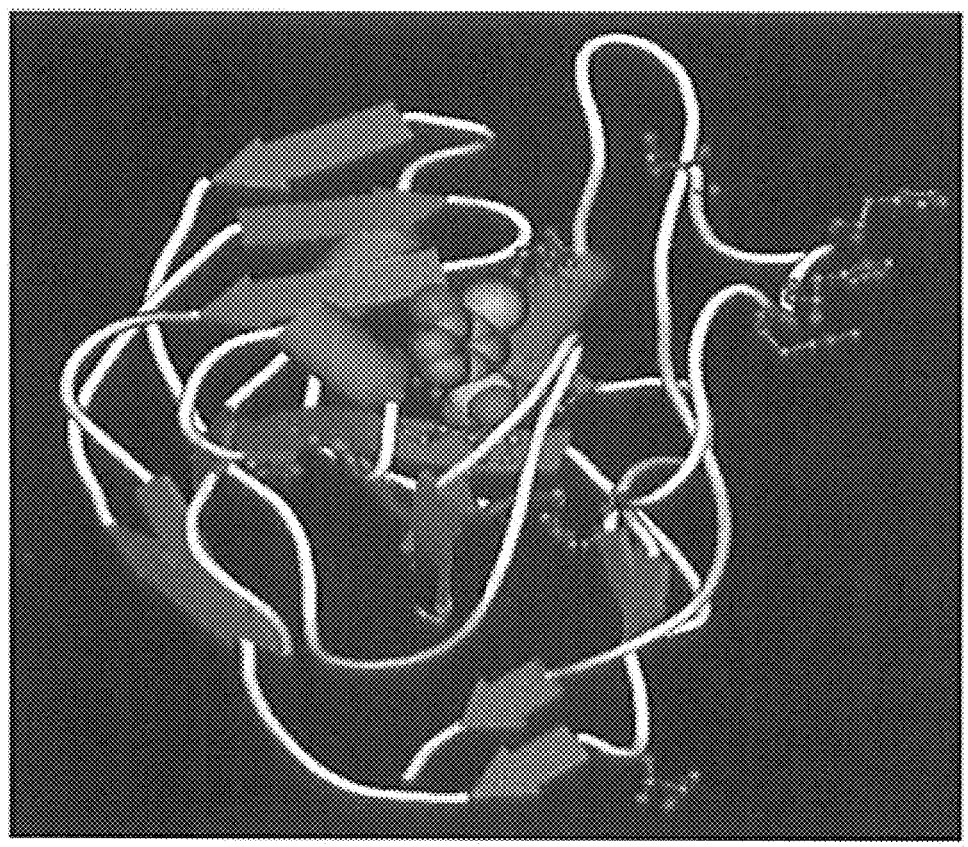
FIG. 1 is a cartoon diagram showing the structure of human carbonic anhydrase.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

The term "pharmaceutical composition" is used herein as commonly known by those skilled in the art and generally indicates a mixture containing ingredients that are compatible when mixed and which may be administered to a patient or biological system, whether human, animal or in vitro, in order to treat a condition or disease. A pharmaceutical composition may cause a degree of toxicity in the patient to whom it is administered but, typically, it would be given in a dosage form and/or amount that does not cause substantial harm to the patient or biological system being treated. Examples of this dichotomy would include pharmaceutical compositions for cancer chemotherapy, which are more toxic for cancer cells than for normal cells but, nevertheless, exert a level of toxicity on the patient's normal cells during treatment. A pharmaceutical composition may include one or more medicinal drugs, which may or may not be prescription drugs. Additionally, the pharmaceutical composition may include carriers, solvents, adjuvants, emollients, expanders, stabilizers and other components, whether these are considered active or inactive ingredients. The skilled will readily understand that the exact makeup of the composition will depend on the intended route of administration to the patient, for example, a composition intended for topical application to the skin will necessarily contain different components than one intended for ophthalmic instillation. Guidance for the skilled in preparing pharmaceutical compositions may be found in the U.S. Pharmacopeia-National Formulary and other recognized treatises in the science of pharmacy.

The figures illustrate the invention disclosed, which comprises inhibition of hCAII, a primary target enzyme for the treatment of glaucoma. Nanoceria, a nontoxic nanoparticle, was functionalized with hCAII inhibitors and was tested as a potential ophthalmic drug delivery tool. We have found various applications of cerium oxide nanoparticles in biotechnology. It was found that treatment with nanomolar concentrations of cerium oxide nanoparticles increases cell longevity[20] and protects the cells from damages caused by X-ray radiation[21] and reactive oxygen species (ROS). These previous studies have revealed that nanoceria particles are nontoxic and exhibit favorable biocompatibility.

Our studies related to use of nanoceria to protect the retina from oxidative stress caused by reactive oxygen species showed that the nanoparticles injected in the vitreous showed efficacy far away in the retina.[22] Moreover, the nanoceria's uptake in human lung fibroblast cells was shown to be faster than the physical transport to the cell[23] suggesting that these particles have favorable diffusive properties. Therefore, a composition of CeO2 nanoparticles was deemed as potentially very good candidate for serving as transport agent for the inhibitors. Since carbonic anhydrase n is a cytosolic enzyme, that is, it is found in cellular cytoplasm, the inhibitor-functionalized nanoceria were synthesized to allow easy entry into living cells.

The first step was to choose a molecule that can attach to the nanoceria and that can inhibit carbonic anhydrase. Carboxybenzene sulfonamide (CBS) (FIG. 2a) was the primary choice on the basis of the literature data, where it is shown that these benzenesulfonamides can serve as inhibitors of carbonic anhydrases and can possess favorable carboxyl groups for attachment.[8,24] It was hypothesized that binding these molecules to the nanoceria would create an effective inhibitor of carbonic anhydrase that can be transferred into the cytosol. Additionally, we also decided to attach a tracking compound, a carboxyfluorescein molecule (FIG. 2b), to visualize the cell permeation property of the nanoparticles through a confocal fluorescence microscope.

The attachment of carboxybenzene sulfonamide and carboxyfluorescein molecules to nanoceria was confirmed using X-ray photoelectron spectroscopy (XPS). The formation of the fluorophore-functionalized nanoparticles was further established through confocal fluorescence microscopy. Finally, the derivatized nanoceria were tested as inhibitors of the recombinant hCAII enzyme. This was accomplished by observing the effect of nanoparticles on the rate of hCAII-catalyzed hydrolysis of the substrate 4-nitrophenyl acetate.[26]

Experimental Section

Figure 3:
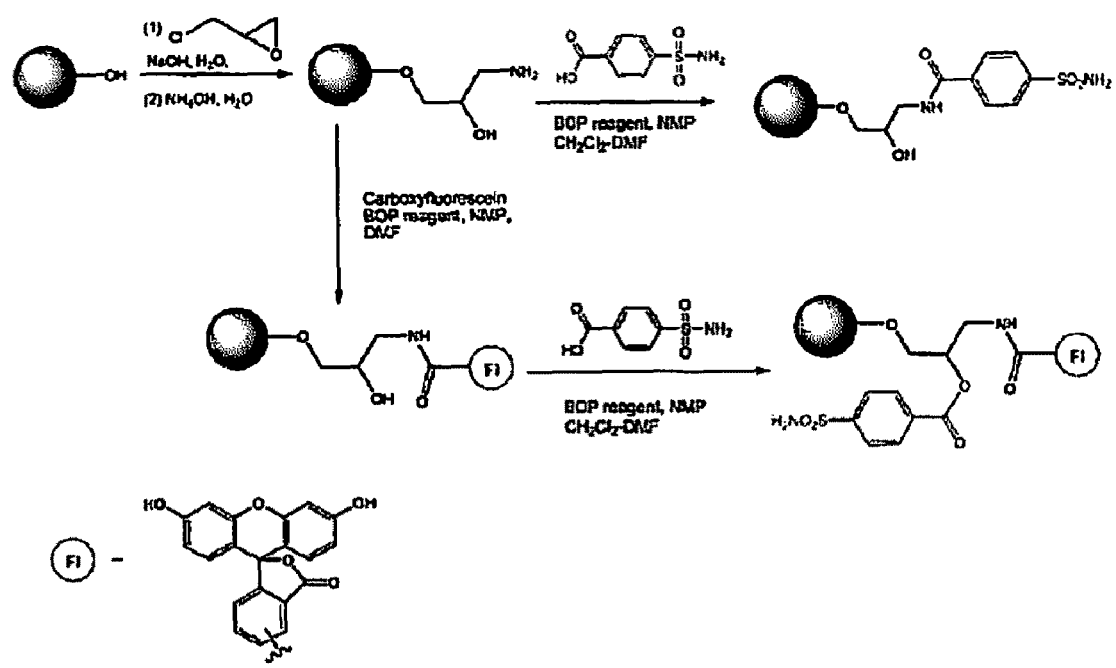
FIG. 3 depicts schemes for synthesis of functionalized nanoceria; (A) for nanoceria-CBS; and (B) for nanoceria-CBS-CBF, according to embodiments of the present invention.

Functionalization of Cerium Oxide Nanoparticles (Scheme 1, FIG. 3).

Reaction of CeO2 Nanoparticles with Epichlorohydrin and Ammonia.

The 250 mg of cerium oxide nanopowder (obtained from Sigma-Aldrich Inc.) was suspended in 10 mL of 0.1 M NaOH solution for 5 min. Then, 5 mL of epichlorohydrin was added, followed by the addition of 0.5 mL of 2 M NaOH. The suspension was stirred at room temperature for 6-8 h. The reaction mixture was then centrifuged, and the supernatant was decanted. The nanoparticles were washed by water followed by centrifugation. This was done until the pH of the water was approximately 7.0. The nanoceria powder was then dried under vacuum. Next, the nanopowder was again suspended in water, 25 mL of 30% ammonium hydroxide solution was added, and the reaction mixture was stirred for 14 h. The product was purified by centrifugation, was washed with water, and was dried under vacuum again.

Reaction with Carboxybenzene sulfonamide and Carboxyfluorescein.

The nanoparticles from the previous step were functionalized with the carboxybenzene sulfonamide and carboxyfluorescein molecules. These molecules (either 200 mg, 1 mmol of the CBS or carboxyfluorescein) were sissolved in 15 mL of dimethylformadide (DMF) and 5 mL of dichloromethane. Three hundred sevent-five microliters (3.5 mM) of N-methylmorpholine (NMP) was added followed by the addition of 442.5 mg (1 mmol) of the benzotriazol-1-yl-oxy-tris-(dimethylamino) phosphonium hexafluorphosphage (BOP) reagent. The reaction mixture was stirred for 10 min at room temperature. The nanoparticles were then added. The mixture was stirred for approximately 20 h at room temperature. The reaction was stopped with 1 mL of water, and the mixture was centrifuged. It was then washed with DMF, water, and acetone three times each to get rid of the unattached carboxyfluorescein and finally was centrifuged. The nanoparticles were finally dried under vacuum.

The carboxyfluorescein-functionalized nanoparticles were taken through the same procedure to attach additional CBS. This resulted in nanoparticles functionalized with carboxybenzene sulfonamide, as well as particles with both the CBS and carboxyfluorescein as shown in Scheme 1.

X-ray Photoelectron Spectroscopy (XPS)

The surface functionalization chemistry of the nanoceria was examined using a 5400 PHI ESCA (XPS) spectrophotometer. The base pressure during the XPS analysis was approximately $10^{-9}$ Torr, and Mg K$\alpha$ X-radiation (1253.6 eV) at a power of 200 W was used. The instrument was calibrated using a standard gold sample with the binding energy at 84.0±0.1 eV for Au ($4f_{7/2}$). All the samples were placed on a carbon tape. Any charging shift produced during the scanning was subtracted by using a binding energy scale with the baseline set at 284.6 eV for the C (1s).[27] The XPS spectra were deconvoluted using PeakFit (version 4) software. The surface concentration of various conjugates was 158 evaluated from the integrated areas of the peaks corresponding to the respective conjugates.

Confocal Fluorescence Microscopy (CFM).

An Olympus 161 Fluoroview IX 81 confocal fluorescence microscope was used. Imaging was performed on prepared slides with nanoceria samples functionalized with carboxyfluorescein. The concentration of nanoceria was optimized to 1 mg/mL of water for imaging. The emission and excitation wavelengths for carboxyfluorescein were determined to be 520 and 480 nm, respectively.

Ultraviolet-Visible Spectrophotometry (UV-vis).

Cary 1E UV-vis spectrophotometer (UV-vis) from Varian Inc. was used to determine the inhibition potential of the nanoceria functionalized with the CBS. The enzyme activity was measured in 25 mM HEPES buffer, pH 7.0 at 25° C., containing 10% acetonitrile. The concentration of hCAII (obtained from Sigma-Aldrich Company) was kept constant at 1 uM for all the experiments. The concentration of the substrate, 4-nitrophenyl acetate (in acetonitrile), was 1 mM for experiments carried out with varying concentrations of functionalized nanoceria and varied between 1 and 5 mM for the kinetic parameter determination studies with constant concentration of the functionalized nanoceria at 0.16667 mg/mL. The initial rates of 4-nitrophenyl acetate hydrolysis by hCAII were monitored spectrophotometrically, at 400 nm, using the Cary Win UV Kinetics application. The molar absorption coefficient, $\epsilon$ of 18 400 M$^{-1}$ cm$^{-1}$, was used to determine the concentration of 4-nitrophenolate formed by hydrolysis, as reported in the literature.[28]

The substrate concentration dependent kinetic data in the absence and presence of functionalized nanoceria inhibitors was presented in the form of double reciprocal plots and was analyzed according to the Michaelis-Menten equation to obtain the $K_m$ and $V_{max}$ values. The inhibitor binding constant, $K_i$, for the functionalized-nanoceria inhibitors was determined according to the following relationship:[29]

$$K_i = \frac{K_m[I]}{K_{m'} - K_m}$$

where, [I] is inhibitor (functionalized nanoceria) concentration; $K_m$ and $K_{m'}$ are Michaelis constants in the absence and presence of the inhibitor, respectively.

Results

The expected functionalization of nanoceria was confirmed by XPS. The attachments of the epichlorohydrin linker, the inhibitor, and the fluorophore were established by examining the high-resolution C (1s) and O (1s) XPS spectra. The attachment of the fluorophore-functionalized nanoparticles was further confirmed by imaging using a confocal fluorescence microscope.

Functionalization Chemistry Using X-ray Photoelectron Spectroscopy (XPS).

The carboxybenzene sulfonamide and carboxyfluorescein were conjugated by first attaching epichlorohydrin to the surface of nanoceria particles. This is a standard $S_N2$ reaction where the oxygen atom of the nanoceria essentially replaces the chlorine atom of the epichlorohydrin.[30] This results in an oxygen atom that bonds the cerium with the carbon of the epichlorohydrin as seen in the first reaction of Scheme 1, as shown in FIG. 3.

In case of nanocrystalline cerium oxide, the O (1s) spectra contain two peaks corresponding to the mixed valence state of Ce ($Ce^{3+}$ and $Ce^{4+}$) present in its crystal lattice. The peak at 530.5 eV corresponds to $Ce^{4+}$ while the higher binding energy peak at about 532.20 eV corresponds to $Ce^{3+}$.[31] The two additional peaks present in the spectra given in FIG. 4a demonstrate that the expected functionalization occurred. These peaks include the O (1s) line of the epichlorohydrin's epoxy group at 533.30 eV and the O—C bond that connects the main part of the epichlorohydrin molecule to the cerium oxide at 534.10 eV.[32] The high-resolution O (1s) XPS spectra thus indicate the successful attachment of the epichlorohydrin molecule to cerium oxide nanoparticles. The loading of epichlorohydrin on the ceria nanoparticles, calculated from the integrated areas of O peaks corresponding to epichlorohydrin to those for $Ce^{3+}$ and $Ce^{4+}$, was evaluated to be 3.18 mmol/gm of $CeO2$.

Ammonia was then used to open up the epoxide ring ($S_N2$ reaction) on the epichlorohydrin molecule to form amine (—$NH_2$) and hydroxyl (—OH) groups available for further reactions (FIG. 3, Scheme 1). The indication that this reaction occurred lies in the diminishment of the peak at 533.30 from FIG. 4a. The new peak at 533.00 eV in FIG. 4b corresponds to the newly formed —OH groups.[32] However, FIG. 4b also confirms that the O—C bond that links the epichlrohydrin molecule bond to the nanoceria remained with the peak at 534.00 eV. Thus, the epichlrohydrin was still attached to the nanoceria and the epoxide ring opened as expected. The integrated area analysis of the peaks confirmed almost 100% ring opening for the epoxide group of the epichlorohydrin conjugated to the cerium oxide nanoparticles.

Figure 2:
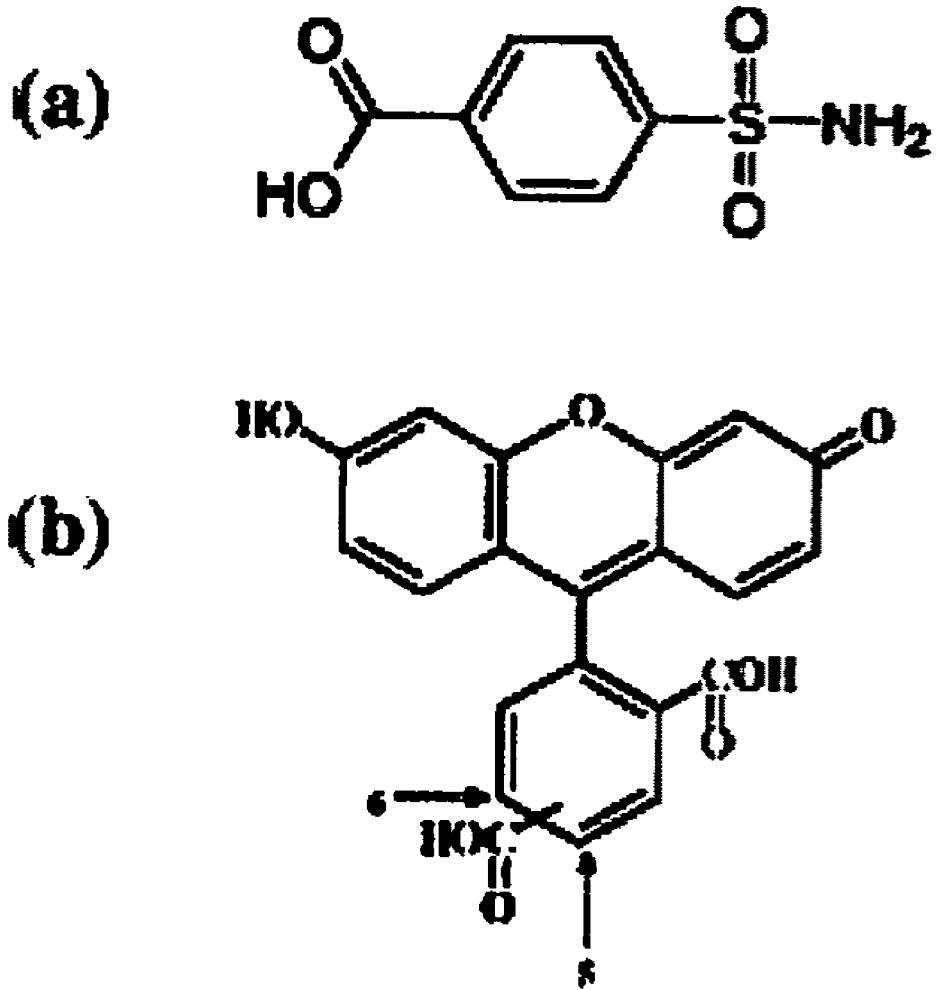
FIG. 2 depicts the molecular structure of (a) carboxybenzene sulfonamide (CBS) and (b) carboxylfluorescein (CBF)

The nanoceria now possessed two functional groups that could be further functionalized by the carboxybenze sulfonamide and carboxyfluorescein molecules. Both of them have carboxyl groups that can react to the available amine and hydroxyl groups from the opened ring of the surface-functionalized nanoceria (FIG. 2). The coupling reactions included standard peptide coupling reagents, N-methyl morpholine (NM)) and benzotriazol-1-yl-oxy-tris (dimethylamino) phosphonium hexafluorophosphate (BOP). The reactions were conducted in dimethylformamide (DMF), a polar aprotic solvent that facilitates the coupling.

The attachment of the inhibitor, CBS, to the amine group was confirmed by the O $1_s$ XPS spectrum in FIG. 4c. The locations of all of the peaks essentially remained the same from the previous spectrum in FIG. 4b except for two additional peaks. These peaks at 531.13 and 531.70 eV correspond to the double-bonded oxygen atoms of the C=O and S=O bonds, respectively, that are part of the CBS. The XPS analysis thus indicated that the inhibitor bonded to the nanoceria particles. The loading yield determined from the deconvoluted peak areas was evaluated to be 3.14 mmol/gm of $CeO_2$ (98.8%).

Instead of the O 1s spectrum, the carbon (C 1s) spectrum was used to confirm the attachment of carboxyfluorescein, because this large molecule shielded many of the oxygen peaks seen in the previous oxygen spectra. FIG. 4d shows the various peaks present in the XPS spectra corresponding to the different C positions in the structure of the carboxyfluorescein functionalized ceria nanoparticles. It confirms that the fluorophore was also attached successfully to the ceria nanoparticles via epichlorohydrin linkage. The XPS peak analysis gave the surface concentration of the fluorophore to be 6.0 mmol/gm of $CeO_2$. The results of the high-resolution XPS spectra for all of the reactions are summarized in Table S 1 of the Supporting Information (not shown but incorporated herein by reference; this material is available to the public free of charge via the Internet at http://pubs.acs.orq a web site of The American Chemical Society).

Confocal Fluorescence Microscopy.

Figure 4:
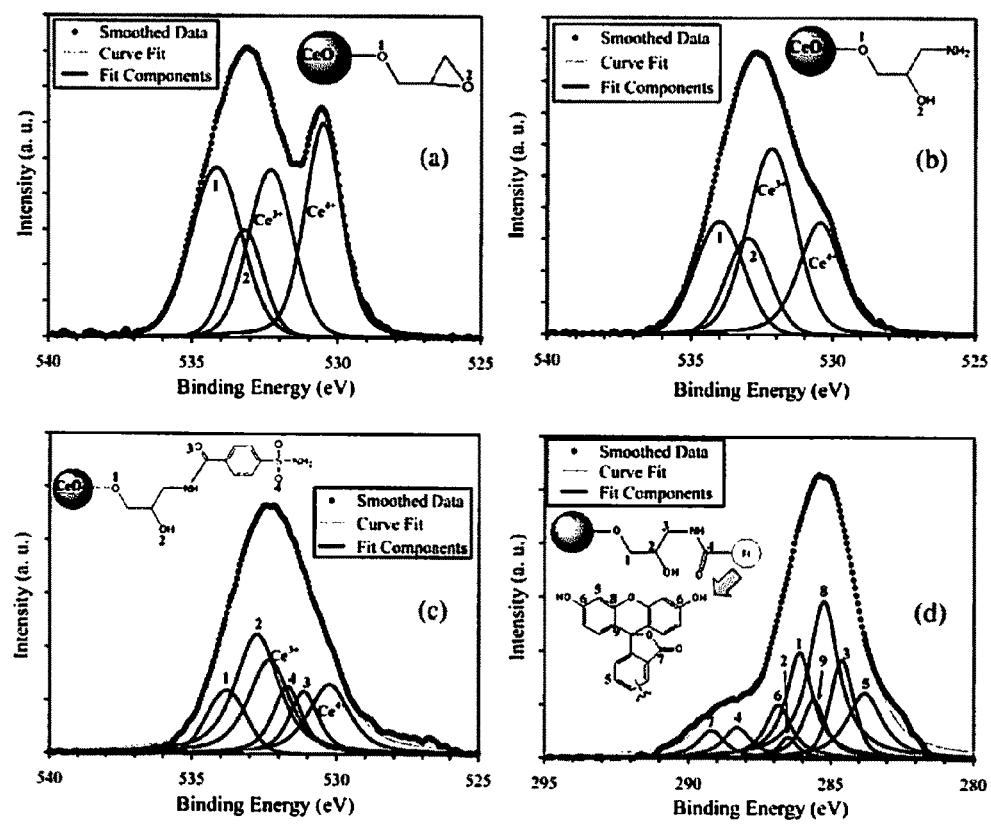
FIG. 4 shows high-resolution XPS spectra for the functionalized nanoceria particles at various conjugation steps; (a) O Is scan for epichlorohydrin-functionalized nanoceria; (b) O Is scan for the opened epoxide ring of epichlorohydrin; (c) O Is scan for carboxybenzene sulfonamide-functionalized nanoceria; and (d) C Is scan for carboxyfluorescein-functionalized nanoceria.
Figure 5:
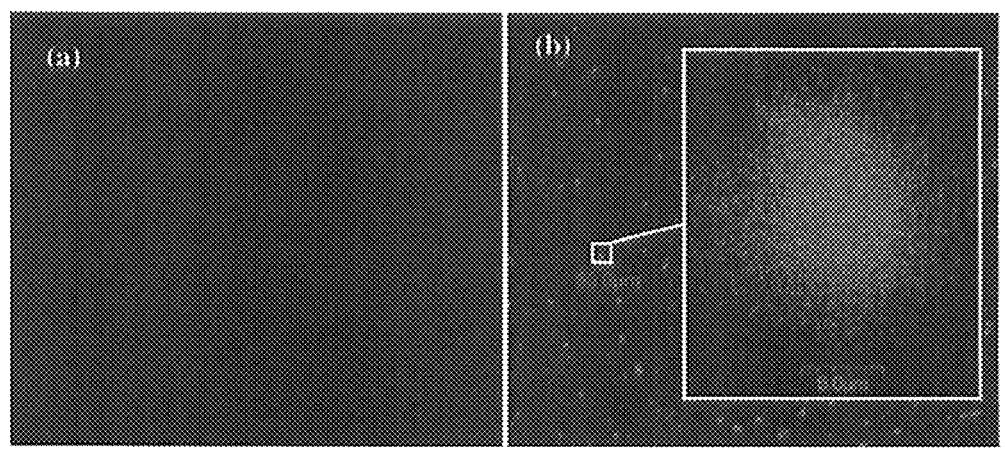
FIG. 5 are images from confocal fluorescence microscopy of (a) bare nanoceria and (b) nanoceria with fluorophores.

Further evidence that the fluorescent molecules bonded was presented in the confocal fluororescence microscopy images. As seen in FIG. 4, the carboxyfluorescein-functionalized nanoparticles were clearly visible under a confocal fluorescence microscope ($\lambda_{ex}$=480 nm; $\lambda_{em}$=520 nm) as green dots while the bare nanoceria resulted in images showing a black background. An individual green dot represents a small agglomerate of the ceria nanoparticles (particle size: 10-20 nm) successfully functionalized with carboxyfluorescein. This further demonstrates that the fluorophores were attached to the nanoceria. The procedure for attaching these fluorescent molecules can be used in future studies to track the nanoceria as they are inserted into living cells. Future studies will involve inserting these particles in vivo and tracking their movement as they approach the expected locations of enzymes.

Inhibition Studies.

The final facet of the study involved determining whether the functionalized nanoceria inhibited the recombinant hCAII enzyme. This was accomplished by observing the effect of nanoparticles on the rate of hCAII-catalyzed hydrolysis of the substrate 4-nitrophenyl acetate. Essentially, the nanoparticles were mixed with a solution of the 4-nitrophenyl acetate and enzyme. The UV-vis spectrophotometer then measured the absorbance values at 400 nm as 4-nitrophenylacetate was hydrolyzed to form 4-nitrophenolate. The change in the absorbance values at different concentrations of nanoceria indicated the inhibiting effect of the conjugated nanoparticles.

Figure 6:
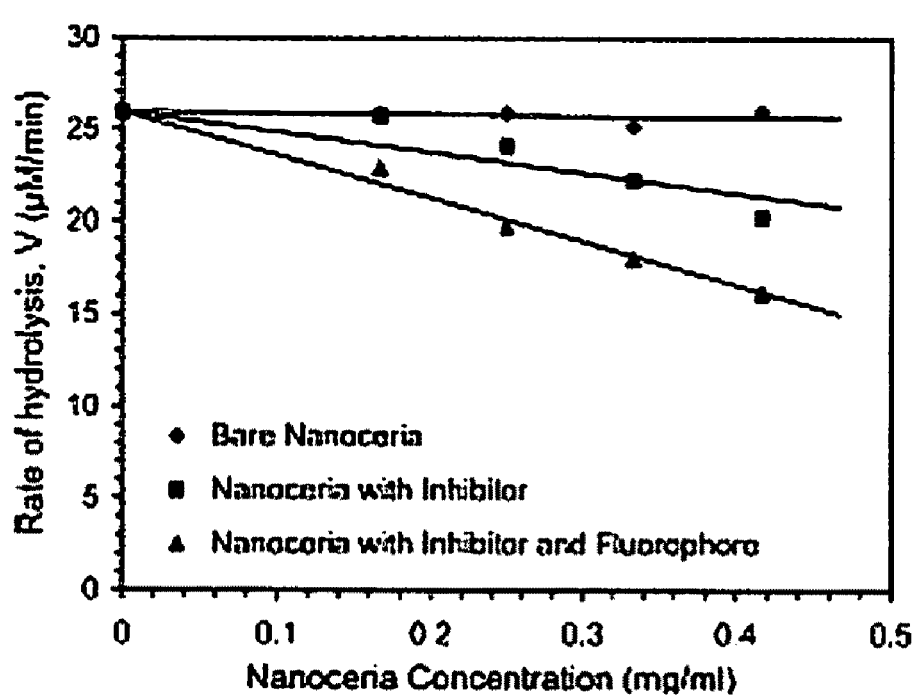
FIG. 6 shows line graphs indicating the rate of hydrolysis of 4-nitrophenyl acetate by hCAII, determined using absorbance change at 400 nm, as a function of the nanoceria concentration.

The declining slopes in FIG. 6 reveal that, when the inhibitor-functionalized nanoceria bound to the active site of hCAII, the rate of formation of 4-nitrophenolate from 4-nitrophenyl acetate decreased. A decrease in the rate of its formation produced a solution that became tinted at a slower rate, which was represented by the decrease in the absorbance values as a function of time (see FIG. 6). hCAII's activity declined with increased concentration of nanoceria, as indicated by the decreasing rate for the hydrolysis of 4-nitrophenyl acetate to 4-nitrophenolate. Bare nanoceria did not affect the rate of hydrolysis of 4-nitrophenyl acetate. When the inhibitor was paired with the fluorophore, the inhibition was better than with nanoceria functionalized only with CBS. The kinetic parameters ($K_m$, $V_{max}$ and $K_i$) for the functionalized nanoceria samples, determined using the double-reciprocal plots, are summarized in Table 1.

TABLE 1

Kinetic Parameters of the hCAII-Catalyzed Reaction in the Absence and Presence of Functionalized-Nanoceria Inhibitors

| inhibitor | $K_m$ (mM) | $V_{max}$ (mM/min) | $K_i$ (mg/mL) |
| --- | --- | --- | --- |
| no inhibitor | 115.23 ± 1.36 | 3.02 ± 0.15 | |
| nanoceria with inhibitor (CBS) | 125.40 ± 0.98 | 3.24 ± 0.08 | 1.89 ± 0.16 |
| nanoceria with inhibitor (CBS) and fluorophore (carboxyfluorescene) | 135.24 ± 1.10 | 3.12 ± 0.10 | 0.96 ± 0.09 |

Discussion

One of the emerging goals of nanotechnology is to functionalize inert and biocompatible materials to impart precise biological functions. Several hybrid organic/inorganic nanoparticles have been described for diagnostic or therapeutic use,[34,35] including quantum dots,[36,37] polymers,[38] and magnetofluorescent nanoparticles.[39] Although many coupling systems have been reported for polymeric nanoparticle conjugation with varying degrees of success,[40,41] the coupling and functionalization of inorganic nanoparticles with biomolecules has only been carried out with a limited number of chemical methods. Niemeyer42 has written an elaborate review on usage of various coupling agents such as citrate, streptavidin, and various other complex linker molecules with amide and carboxylic acid end groups for coupling of inorganic nanoparticles (Au, Ag, ZnS, CdS, $SnO_2$, $TiO_2$, etc.) and biomolecules (proteins, DNA, etc.).

In this disclosure, we have shown the simultaneous conjugation of the hCAII inhibitor, CBS, and the fluorophore, carboxyfluorescein, to cerium oxide nanoparticles via epichlorohydrin as a linker molecule. Epichlorohydrin is a highly reactive compound used in manufacture of epoxy and phenoxy resins. It is also used as a solvent and in the synthesis of glycerol. Anirudhan et al.[43] have developed a new adsorbent system for phosphate removal from wastewaters using epichlorohydrin to modify lignocellulosic residue. Also, it has been used in synthesis of lipopolyhydroxylalkylamines for gene delivery.[44] Weissleder et al. 45 cross-linked the monocrystalline magnetic nanoparticles, consisting of 3 nm core of $(Fe_2O_3)_n(Fe_3O_4)_m$ covered with a layer of dextran, with epichlorohydrin and aminated them by reaction with ammonia to provide primary amine groups for the parallel synthesis of a library comprising 146 nanoparticles decorated with different synthetic small molecules. Similarly, in the present study, epichlohydrin was attached to the ceria nanoparticles via a condensation reaction between the organochloride group from epichlorohydrin and the surface hydroxyl groups of the nanoceria particles and then was aminated to provide primary amine group for conjugation of enzyme inhibitor as well as the fluorophore to the nanoceria particles. The epichlorohydrin may have provided a spacer that allowed the inhibitor to reach the active site of the carbonic anhydrase and to reduce any steric hindrance of the enzyme's interaction with the inhibitors on the surface of the nanoparticles. Furthermore, the inhibition was nearly directly proportional with increased concentration of the functionalized nanoceria inhibitors (FIG. 6). The analysis of the kinetic data conformed to the competitive type of inhibition model. Higher $K_m$ values in the presence of functionalized nanoceria inhibitors than in its absence eliminate the possibility of "noncompetitive inhibition". In conclusion, these results demonstrate that inhibition of the hCAII enzyme can be achieved using nanoceria particles surface-functionalized with CBS.

The aim of the present application is to show that a successful conjugation of the ceria nanoparticles can be carried out using epichlorohydrin as a linker molecule and that such conjugated nanoparticles can be used for hCAII inhibition along with fluorescence-imaging capabilities. The inhibition results may be further enhanced using multiprong surface-binding groups. Our earlier studies in this regard have shown a potential strategy to improve inhibition of hCAII by attaching a surface-histidine recognition group to the inhibitor. Our on-going investigations include the usage of the same conjugation process for multiprong inhibitors of hCAII for improved results.

CONCLUSION

Nanoceria were successfully functionalized and tested as inhibitors for hCAII. High-resolution XPS C 1s and O 1s spectra were effectively utilized to follow the necessary steps in the reaction process. The fluorescence microscope images and quantitative observations further confirmed that the carboxyfluorescein molecules bonded to the nanoceria particles. These results are very promising, and more studies will likely evolve into an inhibition of hCAII in living cells and an effective treatment of glaucoma and other diseases.

Furthermore, inhibitors for other disease associated enzymes can be immobilized on the nanoceria and then applied to the enzymes. The potential applications for functionalized cerium oxide nanoparticles seem limitless as a potential nontoxic drug delivery tool.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed is:

1. A method of treating a patient's eye condition, the method comprising:
   providing a composition containing a plurality of nanoceria particles associated with a drug and suspended in a pharmaceutically acceptable carrier; and
   contacting the patient's eye with the composition.

2. The method of claim 1, wherein the drug comprises an enzyme inhibitor.

3. The method of claim 1, wherein the drug comprises an inhibitor of human carbonic anhydrase.

4. The method of claim 3, wherein the eye condition comprises glaucoma.

5. The method of claim 1, wherein the drug comprises 4-carboxybenzene sulfonamide.

6. The method of claim 5, wherein the eye condition comprises glaucoma.

7. The method of claim 1, wherein contacting comprises a procedure selected from instilling, injecting, diffusing and combinations thereof.

* * * * *